United States Patent [19]
Fujioka et al.

[11] Patent Number: 5,654,317
[45] Date of Patent: Aug. 5, 1997

[54] ANTIARRHYTHMIC AGENT

[75] Inventors: Takafumi Fujioka; Shuji Teramoto; Michiaki Tominaga; Yoichi Yabuuchi, all of Tokushima, Japan

[73] Assignee: Otsuka Pharmaceutical Company, Limited, Tokyo, Japan

[21] Appl. No.: 403,891

[22] PCT Filed: Sep. 10, 1993

[86] PCT No.: PCT/JP93/01294

§ 371 Date: Mar. 17, 1995

§ 102(e) Date: Mar. 17, 1995

[87] PCT Pub. No.: WO94/06427

PCT Pub. Date: Mar. 31, 1994

[30] Foreign Application Priority Data

Sep. 18, 1992 [JP] Japan ................. 4-249694

[51] Int. Cl.$^6$ ........................... A61K 31/47
[52] U.S. Cl. ............... 514/312; 514/314; 546/157
[58] Field of Search ..................... 514/312, 314, 514/350; 546/157

[56] References Cited

U.S. PATENT DOCUMENTS

| | | | |
|---|---|---|---|
| 5,053,514 | 10/1991 | Fujioka et al. | 546/157 |
| 5,266,577 | 11/1993 | Fujioka et al. | 514/312 |
| 5,401,754 | 3/1995 | Fujioka et al. | 514/312 |

FOREIGN PATENT DOCUMENTS 63-290821  11/1988  Japan .

OTHER PUBLICATIONS

Hartzler et al., "Transesophageal Atrial Pacing in the Wolff–Parkinson–White Syndrome", Mayo–Clin–Proc., vol. 52, No. 9, pp. 576–581, Sep. 1977, Abstract Only.

Verdouw et al., "The Effect of Felodipine on Ventricular Fibrillation After Coronary Artery Ligation in the Anaesthetized Pig", Br–J–Pharmacol., vol. 79, No. 1, pp. 6–8, May 1983, Abstract Only.

Krikler, D.M., "Calcium Antagonists and Cardiovascular Disorders", Ann–Cardiol–Angeiol–Paris, vol. 33, No. 8, pp. 513–518, Dec. 1984, Abstract Only.

Leenhardt et al., "Torsades de Pointes with Short Coupling Interval", Arch–Mal–Coeur–Vaiss, 86(5 Suppl) pp. 777–782, May 1993, Abstract Only.

Lucchesi et al., "Antiarrhythmic Versus Antifibrillatory Actions: Inference From Experimental Studies", Am–J–Cardiol., vol. 72, No. 16, pp. 25F–44F, Nov. 26, 1993, Abstract Only.

Coumel et al., "Antiarrhythmic Drugs: How to Evaluate Them?", Am–Heart–J., 127(4 Pt 2) pp. 1119–1125, Apr. 1994, Abstract Only.

Man et al., "Electrophysiologic Effects of Sotalol and Amiodaronein Patients With Sustained Monomorphic Ventricular Tachycardia", 74(11), pp. 1119–1123, Dec. 1, 1994, Abstract Only.

Zhenjiu, Wu et al., "Effects of OPC–18790, a New Positive Inotropic Agent, on Canine Ventricular Arrhythmias", The Japanese J. of Pharmacology, 63(3), Nov. 1993, pp. 399–404.

Cardiovascular actions of OPC–18790: A novel positive inotropic agent with little Chronotropic action. Hosokawa et al. *Heart and Vessels*, 1992.

*Primary Examiner*—John C. Bleutge
*Assistant Examiner*—Robert H. Harrison
*Attorney, Agent, or Firm*—Sughrue, Mion, Zinn, Macpeak & Seas

[57] ABSTRACT

An antiarrhythmic agent which comprises as an active ingredient a carbostyril derivative of the formula:

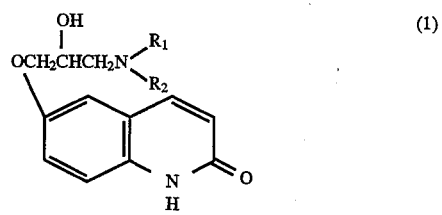

wherein $R_1$ is hydrogen atom or a lower alkyl group, and $R_2$ is a phenyl-lower alkyl group which has optionally 1 to 3 substituents of a lower alkoxy group on the phenyl ring, or a pharmaceutically acceptable salt thereof.

1 Claim, No Drawings

ANTIARRHYTHMIC AGENT

TECHNICAL FIELD

This invention relates to an antiarrhythmic agent, more particularly to an antiarrythmic agent comprising as an active ingredient a carbostyril derivative of the following formula:

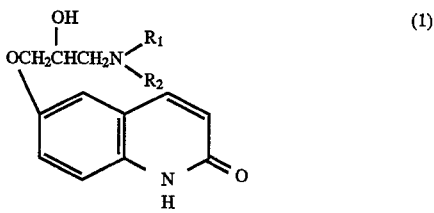

wherein $R_1$ is hydrogen atom or a lower alkyl group, and $R_2$ is a phenyl-lower alkyl group which has optionally 1 to 3 substituents of a lower alkoxy group on the phenyl ring, or a pharmaceutically acceptable salt thereof.

BACKGROUND ART

The carbostyril derivatives of the formula (1) and their salts are known and disclosed, for example, in EP-A-0355583 and U.S. Pat. No. 5,053,514, wherein it is disclosed that these compounds have myocardial contract increasing activity (i.e. positive inotropic activity), coronary blood flow increasing activity, hypotensive activity, an activity of inhibiting blood vessel contract induced by norepinephrine, and antiinflammatory activity and are useful as cardiotonics for the treatment of heart diseases, hypotensives and antiinflammtory. It has also been disclosed in EP-A-0531548 that these compounds have platelet aggregation inhibitory activity, phosphodiesterase inhibitory activity and cerebral blood flow increasing activity and are useful as an agent for treating thrombosis and as a phosphodiesterase inhibitor.

DISCLOSURE OF THE INVENTION

The present inventors have studied on the pharmacological activities and utilities of these carbostyril derivatives and salts thereof and have found that these compounds show excellent antiarrhythmic activity and are useful as an antiarrhythmic agent.

An object of the invention is to provide a novel antiarrhythmic agent. Another object of the invention is to provide a new use of the known carbostyril derivatives of the formula (1) and their salts as an antiarrhythmic agent. A further object is to provide a method for the treatment of arrhythmia by administering an effective amount of the carbostyril derivative (1) or a salt thereof to the subject suffering from arrhythmia.

The each group in the formula (1) denotes as follows.

The "lower alkyl group" denotes a straight chain or branched chain alkyl group having 1 to 6 carbon atoms, such as methyl, ethyl, propyl, isopropyl, butyl, tert-butyl, pentyl, hexyl, and the like.

The "lower alkoxy group" denotes a straight chain or branched chain alkoxy group having 1 to 6 carbon atoms, such as methoxy, ethoxy, propoxy, isopropoxy, butoxy, tert-butoxy, pentyloxy, hexyloxy, and the like.

The "phenyl-lower alkyl group which has optionally 1 to 3 substituents of a lower alkoxy group on the phenyl ring" denotes a phenylalkyl group wherein the alkyl moiety is a straight chain or branched chain alkyl group having 1 to 6 carbon atoms and which has optionally 1 to 3 substituents of a straight chain or branched chain alkoxy group having 1 to 6 carbon atoms on the phenyl ring, such as benzyl, 2-phenylethyl, 1-phenylethyl, 3-phenylpropyl, 4-phenylbutyl, 1,1-dimethyl-2-phenylethyl, 5-phenylpentyl, 6-phenylhexyl, 2-methyl-3-phenylpropyl, 2-(3-methoxyphenyl)ethyl, 1-(4-methoxyphenyl)ethyl, 2-methoxybenzyl, 3-(2-ethoxyphenyl)propyl, 4-(3-ethoxyphenyl)butyl, 1,1-dimethoxy-2-(4-ethoxyphenyl) ethyl, 5-(4-isopropoxyphenyl)pentyl, 6-(4-hexyloxyphenyl) hexyl, 3,4-dimethoxybenzyl, 3,4,5-trimethoxybenzyl, 2,5-dimethoxybenzyl, and the like.

Among the carbostyril derivatives of the formula (1), basic compounds can easily form a salt with conventional pharmaceutically acceptable acids. These acids include, for example, inorganic acids such as sulfuric acid, nitric acid, hydrochloric acid, phosphoric acid, hydrobromic acid, etc., and organic acids such as acetic acid, p-toluenesulfonic acid, ethanesulfonic acid, oxalic acid, maleic acid, fumaric acid, malic acid, tartaric acid, citric acid, succinic acid, benzolic acid, etc. Besides, among the carbostyril derivatives of the formula (1), acidic compounds can easily form a salt with conventional pharmaceutically acceptable basic compounds. These basic compounds include, for example, sodium hydroxide, potassium hydroxide, calcium hydroxide, sodium carbonate, potassium hydrogen carbonate, etc.

The compounds of the formula (1) include optical isomers, and the present invention includes also such optical isomers as the active ingredient.

The compounds of the formula (1) and their salts of the present invention are used in the form of a conventional pharmaceutical preparation. The preparation is prepared by using conventional diluents or carriers such as fillers, thickening agents, binders, wetting gents, disintegrators, surfactants, lubricants, and the like. The pharmaceutical preparations may be selected from various forms in accordance with the desired utilities, and the representative forms are tablets, pills, powders, solutions, suspensions, emulsions, granules, capsules, suppositories, injections (solutions, suspensions, etc.), and the like. In order to form in tablets, there are used conventional carriers such as vehicles (e.g. lactose, white sugar, sodiumchloride, glucose, urea, starches, calciumcarbonate, kaolin, crystalline cellulose, silicic acid, etc.), binders (e.g. water, ethanol, propanol, simple syrup, glucose solution, starch solution, gelatin solution, carboxymethyl cellulose, shellac, methyl cellulose, potassium phosphate, polyvinylpyrrolidone, etc.), disintegrators (e.g. dry starch, sodium arginate, agar powder, laminaran powder, sodium hydrogen carbonate, calcium carbonate, polyoxyethylene sorbitan fatty acid esters, sodium laurylsulfate, stearic monoglyceride, starches, lactose, etc.), disintegration inhibitors (e.g. white sugar, stearin, cacao butter, hydrogenated oils, etc.), absorption promoters (e.g. quaternary ammonium base, sodium laurylsulfate, etc.), wetting agents (e.g. glycerin, starches, etc.), adsorbents (e.g. starches, lactose, kaolin, bentonite, colloidal silicates, etc.), lubricants (e.g. purified talc, stearates, boric acid powder, polyethylene glycol, etc.), and the like. Moreover, the tablets may also be in the form of a conventional coated tablet, such as sugar-coated tablets, gelatin-coated tablets, enteric coated tablets, film coating tablets, or double or multiple layer tablets. In the preparation of pills, the carriers include vehicles (e.g. glucose, lactose, starches, cacao butter, hydrogenated vegetable oils, kaolin, talc, etc.), binders (e.g. gum arabic powder, tragacanth powder, gelatin, ethanol, etc.), disintegrators (e.g. laminaran, agar, etc.), and the like. In the preparation of suppositories, the carriers include, for example, polyethylene glycol, cacao butter, higher alcohols, higher alcohol esters, gelatin, semi-synthetic glycerides, and the like. Capsules can be prepared by charging a mixture of the compound of this invention with the above carriers into hard gelatin capsules or soft capsules in a usual manner. In the preparation of injections, the solutions, emulsions or suspensions are sterilized and are preferably made isotonic with the blood. In the preparation of these solutions, emulsions and suspensions, there are used conventional diluents, such as water, macrogol, ethyl alcohol, propylene glycol, ethoxylated isostearyl alcohol, polyoxylated isostearyl alcohol, polyoxyethylene sorbitan fatty acid esters, and the like. In this case, the pharmaceutical preparations may also be incorporated with sodium chloride, glucose or glycerin in an amount sufficient to make them isotonic, and may also be incorporated with conventional solubilizers, buffers, anesthetizing agents. Besides, the pharmaceutical preparations may optionally be incorporated with coloring agents, preservatives, perfumes, flavors, sweetening agents, and other medicaments, if desired.

The amount of the active compound to be incorporated into the antiarrhythmic agent of this invention is not specified but may be selected from a broad range, but it is usually in the range of 1 to 70% by weight, preferably about 1 to 30% by weight.

The antiarrhythmic preparation of this invention may be administered in any method, and suitable method for administration may be determined in accordance with various forms of preparation, ages, sexes and other conditions of the patients, the degree of severity of diseases, and the like. For example, tablets, pills, solutions, suspensions, emulsion, granules and capsules are administered orally. The injections are intraveneously administered alone or together with a conventional auxiliary liquid (e.g. glucose, amino acid solutions), and further are optionally administered alone in intramuscular, intracutaneous, subcutaneous, or intraperitoneal route, if desired. Suppositories are administered in intrarectal route.

The dosage of the antiarrhythmic agent of this invention may be selected in accordance with the usage, ages, sexes and other conditions of the patients, the degree of severity of the diseases, and the like, but is usually in the range of about 0.1 to 10 mg of the active compound of this invention per 1 kg of body weight of the patient per day. The active compound is preferably contained in an amount of about 1 to about 200 mg per the dosage unit.

BEST MODE FOR CARRYING OUT THE INVENTION

The present invention is illustrated by teh following pharmacological experiment and preparations.

Pharmacological Experiment

The antiarrhythmic activity of the test compound was measured by using an arrhythmic model in dog which showed ventricular tachycardia induced by digitalis. That is, mongrel dogs weighing 9–13 kg were anesthetized with pentobarbital (30 mg/kg, i.v.) and vagotomized at both sides under artificial respiration. A cannula for measuring blood pressure was inserted into the right femoral artery and a cannula for administering a drug was inserted into the right femoral vein. The standard lead II electrocardiogram and also the atrial electrogram from a catheter with electrode set at the right atrium were recorded.

When the experimental dogs became stable, ouabain (40 µg/kg) was intravenously injected, followed by an additional 10 µg/kg at every 20 minutes until stable ventricular tachycardia was produced. When stable venticular tachycardia was obtained (ouabain: 70–90 µg/kg in total), the test compound was administered, and 10, 30 and 60 minutes after the administration of test compound, the severity of arrhythmia was measured. The severity of arrhythmia was expressed by the arrhythmic ratio which was calculated by the following formulae:

$$\text{Arrhythmic ratio} = \frac{\text{Number of ventricular ectopic beats}}{\text{Total heart beats}}$$

The test compound was 6-[3-(3,4-dimethoxybenzyl)-amino-2-hydroxypropoxy]carbostyril which was administered in an amount of 3 mg/kg.

The results in six dogs were evaluated by the following criteria and are shown in Table 1.

Effective: the arrhythmic ratio decreased in 0.25 or more by administration of a test compound.

Somewhat effective: the arrhythmic ratio decreased in the range of 0.1 to less than 0.25 by administration of a test compound.

Unchanged: the arrhythmic ratio did not changed or decreased in less than 0.1 by administration of a test compound.

Becoming worse: the arrhythmic ratio increased by administration of a test compound.

TABLE 1

|  | Effective | Unchanged | Becoming worse |
| --- | --- | --- | --- |
| Number of dogs | 4 | 2 | 0 |

In four dogs which were effective, the ratio of arrhythmia varied after administration of the test compound as shown in the following Table 2.

TABLE 2

|  | Before admin. | 10 min. after admin. | 30 min. after admin. | 60 min. after admin. |
| --- | --- | --- | --- | --- |
| Ratio of arrhythmia | 1 | 0.49 ± 0.27 | 0.37 ± 0.22 | 0.28 ± 0.22 |

| Preparation 1 | |
| --- | --- |
| 6-[3-(3,4-Dimethoxybenzyl)amino-2-hydroxy-propoxy]carbostyril hydrochloride | 5 mg |
| Starch | 132 mg |
| Magnesium stearate | 18 mg |
| Lactose | 45 mg |
| Totally | 200 mg |

Tablets containing the above components in the indicated amounts per one tablet are prepared by a conventional method.

| Preparation 2 | |
|---|---|
| 6-[3-(3,4-Dimethoxybenzyl)amino-2-hydroxy-propoxy]carbostyril hydrochloride | 500 mg |
| Polyethylene glycol (molecular weight: 4000) | 0.3 g |
| Sodium chloride | 0.9 g |
| Polyoxyethylene sorbitan monooleate | 0.4 g |
| Sodium metabisulfite | 0.1 g |
| Methyl-paraben | 0.18 g |
| Propyl-paraben | 0.02 g |
| Distilled water for injection | 100 ml |

The above parabens, sodium metabisulfite and sodium chloride are dissolved in distilled water with stirring at 80° C. The solution thus obtained is cooled to 40° C., and the active compound of this invention and further polyethylene glycol and polyoxyethylene sorbitan monooleate are dissolved in the solution. To the solution is added distilled water for injection to adjust to the desired volume, and the solution is sterilized by fitering with an appropriate filter paper and is entered into an ampoule (1 ml per each ampoute) to give an injection preparation.

INDUSTRIAL APPLICATION

The antiarrhythmic agent of this invention is useful for the prophylaxis and treatment of arrhythmia in human being.

We claim:

1. A method for the prophylaxis or treatment of ventricular tachycardia, which comprises administering an effective amount of a carbostyril derivative of the following formula (1) or a pharmaceutically acceptable salt thereof:

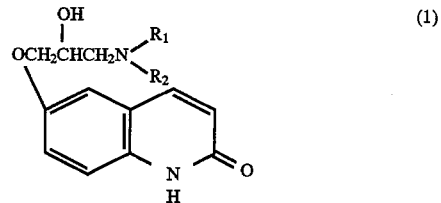

wherein $R_1$ is a hydrogen atom, and $R_2$ is a phenyl ($C_1$-$C_6$) alkyl group which has optionally 1 to 3 substituents of a ($C_1$-$C_6$) alkoxy group on the phenyl ring, to a subject suffering from ventricular tachycardia, wherein said carbostyril derivative of formula (I) is 6-[3-(3,4-dimethoxybenzyl)amino-2-hydroxypropoxy]-carbostyril.

* * * * *